United States Patent
Albano et al.

(10) Patent No.: US 6,350,786 B1
(45) Date of Patent: Feb. 26, 2002

(54) STABLE COMPLEXES OF POORLY SOLUBLE COMPOUNDS IN IONIC POLYMERS

(75) Inventors: Antonio A. Albano; Wantanee Phuapradit, both of Clifton; Harpreet K. Sandhu, West Orange; Navnit Hargovindas Shah, Clifton, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/391,060

(22) Filed: Sep. 7, 1999

Related U.S. Application Data

(60) Provisional application No. 60/136,531, filed on May 28, 1999, and provisional application No. 60/101,336, filed on Sep. 22, 1998.

(51) Int. Cl.[7] .......................... A61K 47/32; A61K 47/38
(52) U.S. Cl. ................. 514/772.4; 514/781; 514/772.6; 424/465
(58) Field of Search ........................ 514/772.4; 424/465

(56) References Cited

U.S. PATENT DOCUMENTS

| | | |
|---|---|---|
| 4,344,934 A | * 8/1982 | Martin ........................ 424/310 |
| 5,281,420 A | 1/1994 | Kelm et al. |
| 5,494,683 A | 2/1996 | Liversidge et al. |
| 5,977,163 A | 11/1999 | Li et al. |
| 6,048,887 A | 4/2000 | Dhingra et al. |
| RE36,736 E | 6/2000 | Davis |
| 6,110,924 A | 8/2000 | Bosies et al. |
| 6,229,011 B1 | 5/2001 | Chen et al. |

FOREIGN PATENT DOCUMENTS

| | | |
|---|---|---|
| WO | 96/35414 | 11/1996 |
| WO | 98/04551 | 2/1998 |
| WO | 99/47518 | 9/1999 |

OTHER PUBLICATIONS

J.L Ford The Current Status of Dispersions pp. 69–88 Pharm. Acta Helv. 61, NR. 3, 1986.*
Chiou et al J. Pharm. Sciences vol. 60. No. 9 pp. 1281–1302, Sep. 1971.*
L. Lachman et al., The Theory and Practice of Industrial Pharmacy, Chapter 2, p. 45 (1986).
M. Yoshioka et al., Journal of Pharmaceutical Sciences, 83(12):1700–1705 (1994).
P.P. Constantinides, Pharmaceutical Research, 12(11): 1561–1572 (1995).
H.G. Britain, Physical Characterization of Pharmaceutical Solids, Drugs and the Pharmaceutical Sciences, vol. 70 (Marcel Dekker, Inc., N.Y., 1995).
Leuner, C., et al., European Journal of Pharmaceuticals and Biopharmaceuticals—Improving Drug Solubility for Oral Delivery using Solid Dispersions, vol. 50 (2000) pp. 47–60.

* cited by examiner

*Primary Examiner*—Thurman K. Page
(74) *Attorney, Agent, or Firm*—George W. Johnston; Patricia S. Rocha-Tramaloni

(57) ABSTRACT

Stable water-insoluble complexes of poorly soluble compounds molecularly dispersed in water-insoluble ionic polymers are disclosed. Useful insoluble ionic polymers have a molecular weight greater than about 80,000 D and a glass transition temperature equal to or greater than about 50°. The compounds are microprecipitated in the ionic polymers in amorphous form. The complexes according to the present invention significantly increase the bioavailability of poorly soluble therapeutically active compounds.

33 Claims, 7 Drawing Sheets

(7 of 7 Drawing Sheet(s) Filed in Color)

STABLE COMPLEXES OF POORLY SOLUBLE COMPOUNDS IN IONIC POLYMERS

This application claims benefit to Provisional Application No. 60/101,336 filed Sep. 22, 1998, which claims benefit to Provisional Application No. 60/136,531 filed May 22, 1999.

BACKGROUND OF THE INVENTION

The present invention provides pharmaceutical compositions comprising a stable water-insoluble complex composed of an amorphous therapeutically active compound (e.g. a drug) dispersed in an ionic polymer. The complexes according to the present invention provide significant increases in bioavailability of poorly soluble therapeutically active compounds.

The bioavailability of a therapeutically active compound is generally affected by (i) the solubility/dissolution rate of the compound, and (ii) the partition coefficient/permeability of the compound through a subject's gastrointestinal membrane. The major cause of poor bioavailability of a therapeutically active compound is the poor solubility/dissolution rate of said compound. Poor bioavailability is also often accompanied with undesirably high rates of patient variability and unpredictable dose/therapy effects due to erratic absorption of the therapeutically active compound (e.g. drug) by the patient.

Several techniques are used to improve the bioavailability of poorly soluble therapeutically active compounds. These techniques are summarized below.

1. Particle Size Reduction

A poorly soluble therapeutically active compound often is mechanically ground to reduce the particle size of the compound and thereby increase the surface area. See Lachman et al., The Theory and Practice of Industrial Pharmacy, Chapter 2, p. 45 (1986). Particle size reduction into micron size particles can be achieved using a jet mill. The mean particle size obtained by the jet mill is typically in the range of 1–10 $\mu$m. Similarly, wet milling of a therapeutically active compound in the presence of protective colloids or polymers typically yields particle sizes of compound in the range of about 300–800 nm. According to this technique, a therapeutically active compound and a polymer are dispersed in water and ground by grinding media such as tiny beads (0.2–0.5 mm). See U.S. Pat. No. 5,494,683. Particle size reduction however, can only improve the dissolution rate of the therapeutically active compound, but not the total amount of compound in solution at equilibrium.

2. Solid Dispersion 2.1 Fusion Method

According to this technique, a therapeutically active compound is dispersed into a non-ionic polymer to form a solid dispersion. Typically, the non-ionic polymer (e.g. Pluronic® and Polyethylene Glycol) is melted to a temperature above its melting point and the therapeutically active compound is dissolved, with stirring, into the molten polymer. See U.S. Pat. No. 5,281,420. The resulting molten mass is then cooled to room temperature. As a result of this process, the therapeutically active compound is fused into the polymer and on cooling, precipitates out in amorphous form. The amorphous form of the compound generally has a faster dissolution rate then the initial crystalline form of the compound. Thus, by rendering the compound in amorphous form this process improves bioavailability. However, due to the greater aqueous solubility and low melting point of non-ionic polymers, the amorphous form of the therapeutically active compound, can not maintain its stability and eventually converts back to the crystalline form after exposure to high humidity and elevated temperatures often encountered during long term storage. See Yoshioka et al., J. Pharm. Sci. 83:1700–1705 (1994). Therefore, this technique is not suitable for most dosage forms of therapeutically active compounds, and certainly not for those therapeutically active compounds having poor solubility.

2.2 Co-precipitation

In another existing method for improving the bioavailability of a poorly soluble therapeutically active compound, the compound and a non-ionic hydrophilic polymer, such as polyvinyl pyrrolidone, are dissolved in an organic solvent. The solvent is removed by evaporation during which the therapeutically active compound precipitates into the hydrophilic polymer matrix. See, H. G. Britain, Physical Characterization of Pharmaceutical Solids, Drugs and the Pharmaceutical Sciences, Vol. 70 (Marcel Dekker, Inc., N.Y., 1995). Due to the hygroscopic nature and aqueous solubility of the polymer, this type of polymer does not protect the amorphous form of the therapeutically active compound from heat and moisture. Thus, the therapeutically active compound in the hydrophilic polymer matrix does not stay in amorphous form and eventually converts to a crystalline form during storage. Therefore, this approach also is not practical to improve the bioavailability of poorly soluble therapeutically active compounds.

3. Self-Emulsifying Drug Delivery System (SEDDS)

In this system, a therapeutically active compound is dissolved in a mixture of a suitable oil and emulsifier. The resultant lipid formulation, upon exposure to gastrointestinal fluids, forms a very fine emulsion or microemulsion. Due to high surface area of the oil globules, the bioavailability of a poorly soluble therapeutically active compound dissolved in such oil is significantly increased. See, P. P. Constantinides, Pharm. Res. 12(11): 1561–1572 (1995). The key requirement for use of this system is that the therapeutically active compound must be soluble in oil and once dissolved in oil, must remain in stable form in the solution. SEDDS is thus not a useful alternative for most therapeutically active compounds due to the limited solubility and unsatisfactory stability of these compounds in an oil-based solution.

We have surprisingly found that when a poorly soluble therapeutically active compound (typically in crystalline form) is molecularly dispersed in a water-insoluble ionic polymer having a molecular weight greater than about 80,000 D and a glass transition temperature equal to or greater than about 50° C., the physical stability of the compound (now in amorphous form) is maintained for long periods of time even under high humidity and temperature storage conditions. Due to the high molecular weight and high glass transition temperature of the ionic polymer, as well as its relative insolubility in water, the ionic polymer immobilizes the therapeutically active compound in its amorphous form thereby providing excellent stability of compound which is superior to that afforded by currently available methods. In addition, due to the increased solubility of the compound in the compound/polymer complex, the bioavailability of the therapeutically active compound is also significantly increased. This method is therefore particularly useful for improving the bioavailability of poorly soluble therapeutically active compounds.

SUMMARY OF THE INVENTION

The present invention provides a pharmaceutical composition comprising a stable, water-insoluble complex composed of a carrier macromolecule that is a water-insoluble ionic polymer having a molecular weight greater than about 80,000 D and a glass transition temperature equal to or greater than about 50° C., and an amorphous therapeutically active compound, wherein the therapeutically active compound is incorporated or dispersed in the ionic polymer in stable amorphous form to yield a compound/polymer complex. Another aspect of this invention is the water-insoluble compound/polymer complex. The complex of the invention is formed by the microprecipitation of the therapeutically active compound in the ionic carrier.

The compound/polymer complex of the invention may be in the form of a solid (e.g. a paste, granules, a powder) which can be filled into capsules or compressed into tablets. The powdered form of the complex may also be pulverized or micronized sufficiently to form stable liquid suspensions or semi-solid dispersions. The complex of the invention may be sterilized, such as by gamma irradiation or electron beam irradiation, prior to administration in vivo for parenteral applications.

BRIEF DESCRIPTION OF THE DRAWINGS

The file of this patent contains at least one drawings executed in color.

DETAILED DESCRIPTION OF THE INVENTION

Figure 1:
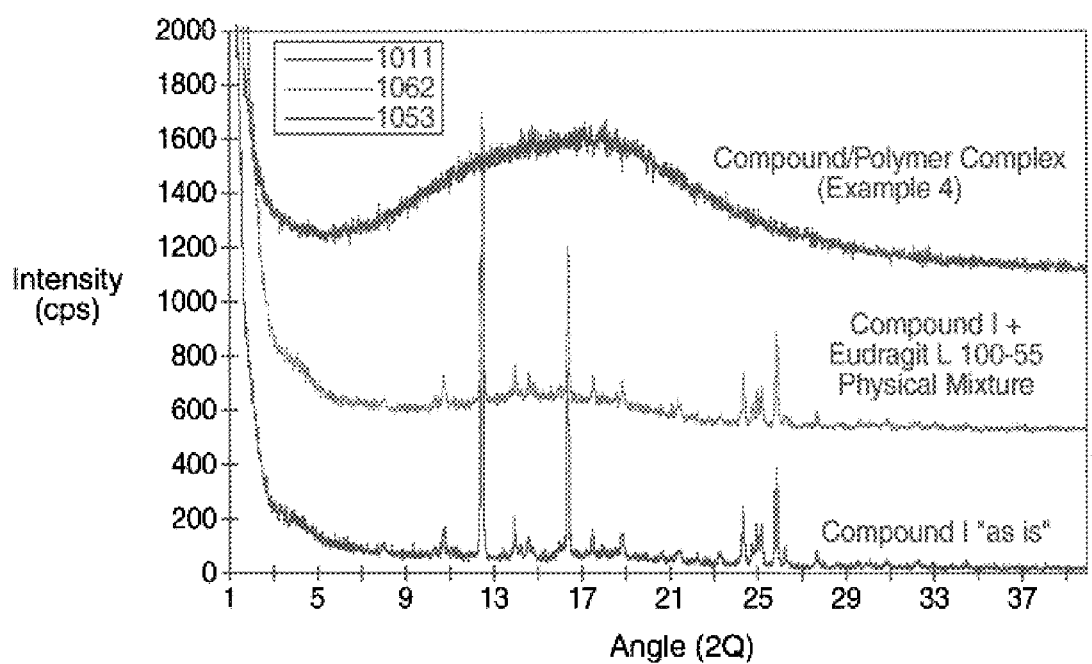
FIG. 1 is a powder x-ray diffraction pattern of the compound/polymer complex of Example 4 compared to the bulk drug alone and compared to drug and polymer physical mixture.

This invention relates to a stable water-insoluble complex composed of a water-insoluble ionic polymer carrier having a molecular weight greater than about 80,000 D and a glass transition temperature equal to or greater than about 50° C. and a therapeutically active compound in stable amorphous form. This invention also relates to methods of making such complexes and pharmaceutical formulations including such complexes. The advantage of the complexes of the invention include the ability to increase substantially the bioavailability of relatively insoluble therapeutically active compounds and the ability for delivery of such compounds for prolonged periods of time (that is, a sustained release of such compounds into the bloodstream).

As used herein, the following terms shall have the following meanings.

"Compound/polymer complex" or "water-insoluble complex" refer to a physically stable product that forms upon the concurrent precipitation ("microprecipitation") of a therapeutically active compound and a water-insoluble ionic polymer according to the methods described herein.

"Dispersed" means random distribution of a therapeutically active compound throughout an ionic polymer.

"Dissolution Rate" means the speed with which a particular compound dissolves in physiological fluids in vitro.

"Ionic polymer" or "ionic carrier polymer" includes both anionic (negatively charged) and cationic (positively charged) polymers.

"Microprecipitation" means any method by which a compound, in particular a therapeutically active compound, is molecularly dispersed in a polymer.

"Molecularly dispersed" means that the therapeutically active compound(s) is present in the polymer in a final state of subdivision. See, e.g., M. G. Vachon et al., J. Microencapsulation 14(3): 281–301 (1997); M. A. and Vandelli et al., J. Microencapsulation 10(1): 55–65 (1993).

"Patient" refers to a human subject.

"Poorly soluble therapeutically active compound" refers to therapeutically active compounds (e.g. drugs) having an aqueous solubility of less than about 1 mg/mL, often less than about 100 µg/mL.

One aspect of the present invention pertains to pharmaceutical compositions comprising a stable water-insoluble complex composed of a carrier macromolecule that is an ionic polymer and a therapeutically active compound that is stable in its amorphous form. The use of such compound/polymer complex is particularly preferable when the compound is otherwise poorly soluble making it difficult to obtain desirable oral bioavailability of said compound.

According to the present invention, when poorly soluble crystalline therapeutically active compound and a water-insoluble ionic polymer having a molecular weight greater than about 80,000 D and a glass transition temperature equal to or greater than about 50° C. are microprecipitated, the compound is molecularly dispersed in amorphous form, into the ionic polymer producing a stable, water insoluble complex. Microprecipitation may be accomplished, for example, by any one of the following methods, each of which is further described infra:

a) Spray Drying or Lyophilization Method
b) Solvent-Controlled Precipitation
c) pH-Controlled Precipitation
d) Hot Melt Extrusion Process
e) Supercritical Fluid Technology Once the therapeutically active compound is so dispersed in the ionic polymer, it retains its amorphous structure even during long term storage, that is, it is "stable". In addition, the ionic polymer protects the compound from detrimental external environmental factors such as moisture and heat, thereby retaining increased solubility and consequent increased bioavailability.

A therapeutically active compound that is contained in a complex amorphous form according to the invention has significantly increase bioavailability in comparison to said compound in its crystalline form and is highly stable over a prolonged period of time. In addition, due to a controlled dissolution rate of the complex in the gastrointestinal fluids, the complex affords sustained release characteristics for the therapeutically active compound dispersed in the compound/polymer complex.

This invention is useful with any therapeutically active compound, but is especially useful for therapeutically active compounds having aqueous solubilities of less than about 1 mg/mL, and especially for compounds having less then 100 µg/mL. Such poorly soluble therapeutically active compounds include, for example, retinoids and protease inhibitors. In particular, this invention is especially useful with the following therapeutic compounds:

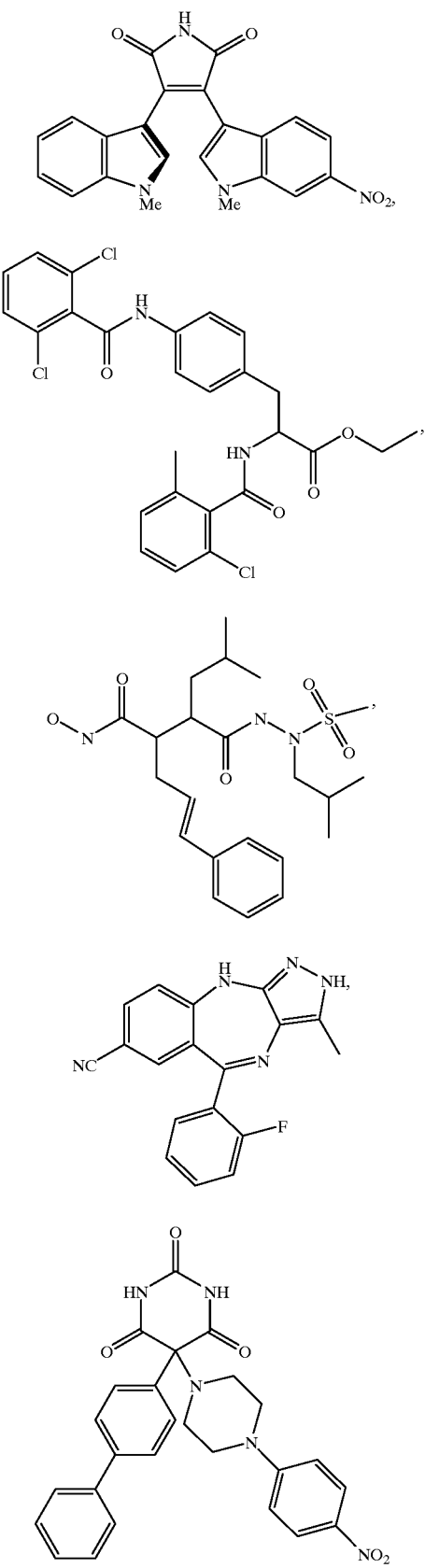

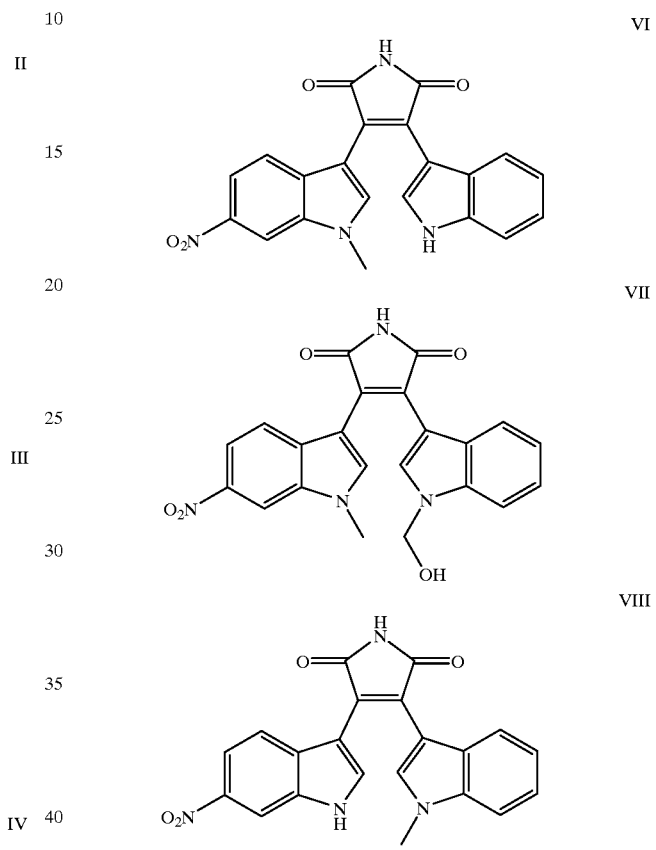

In its crystalline form, Compound I above has extremely poor aqueous solubility (<10 μ/mL) and bioavailability.

This invention is also useful with the compound tolcapone (marketed by Roche Laboratories Inc. under the brand name Tasmar®), the compound 13cis-retinoic acid (commercially from available from Roche Laboratories Inc. under the brand name ACCUTANE®), the compound saquinavir (marketed by Roche Laboratories Inc. as FORTOVASE™), and with the following compounds:

The ionic polymers suitable for use in accordance with this invention are either cationic or anionic polymers, have a molecular weight of above about 80,000 D, a glass transition temperature equal to or greater than about 50° C., are relatively insoluble in water and preferably have pH-dependent solubility. Examples of such polymers include polyacrylates (e.g. Eudragit®, Rohm America), chitosan, Carbopol® (BF Goodrich), polyvinyl acetate phthalate, cellulose acetate phthalate, polycyanoacrylates, hydroxypropylmethyl cellulose phthalate, cellulose acetate terphthalate, hydroxypropyl methyl cellulose acetyl succinate, carboxy methyl cellulose and low substituted hydroxy propyl cellulose. The water-insoluble complexes according to present invention may also be comprised of mixtures of two or more above-described ionic polymers (see, e.g. Examples 9 and 10).

Particularly preferred anionic polymers include Eudragit® L100-55 (methacrylic acid and ethyl acrylate copolymer) and Eudragit® L100 or Eudragit® S100 (methacrylic acid and methyl methacrylate copolymers), all of which are available from Rohm America. Eudragit® L100-55 is soluble at a pH above 5.5 and practically insoluble at pH below 5.5. The molecular weight of Eudragite L100-55 is approximately 250,000 D and the glass transition temperature is 110° C. Eudragit® L100 is soluble at pH above 6 and practically insoluble at pH below 6. The molecular weight of Eudragit® L100 is approximately 135,000 D and the glass transition temperature is about 150° C. Eudragit® S100 is soluble at pH above 7 and practically insoluble at pH below 7. The molecular weight of Eudragit® S100 is approximately 135,000 D and the glass transition temperature is about 160° C.

Particularly preferred cationic polymers include Eudragit® E (Rohm America), which is a copolymer of dimethylaminoethylmethacrylate and neutral methacrylic esters. This polymer is soluble up to pH 4 and is practically insoluble at a pH above 4. The molecular weight of Eudragit® E is approximately 150,000 D and the glass transition temperature is about 50° C.

Pharmaceutical compositions of the present invention comprising the water-insoluable complexes of the invention may be manufactured in a manner that is known in the art, e.g. by means of conventional mixing, milling, encapsulating, dissolving, compressing, granulating, or lyophilizing processes. In addition to the water-insoluble complexes, these pharmaceutical compositions may also include therapeutically inert, inorganic or organic carriers ("pharmaceutically acceptable carriers"), other than the ionic polymer, and/or excipients. Pharmaceutically acceptable carriers for tablets, coated tablets, dragees and hard gelatin capsules include lactose, maize starch or derivatives thereof, talc, stearic acid or its salts. Suitable carriers for soft gelatin capsules include vegetable oils, waxes, fats, and semi-solid or liquid polyols.

The pharmaceutical compositions of the invention may also contain preserving agents, solubilizing agents, stabilizing agents, wetting agents, emulsifying agents, sweetening agents, coloring agents, flavoring agents, salts for varying the osmotic pressure, buffers, coating agents or antioxidants. These compositions may also contain additional therapeutically active compounds or more than one therapeutically active compound/polymer complex.

METHODS OF PREPARATION

In one embodiment of the present invention, water-insoluble complexes of the invention are prepared using one of the following methods:

a) Spray Drying or Lyophilization Method

The therapeutically active compound and the ionic polymer are dissolved in a common solvent having a low boiling point, e.g., ethanol, methanol, acetone, etc. By means of spray drying or lyophilization, the solvent is evaporated, leaving the therapeutically active compound microprecipitated in amorphous form in the ionic polymer matrix. This technique is not preferable for those therapeutically active compounds that do not have adequate solubility (>5%) in the preferred solvents.

b) Solvent Controlled Precipitation

The therapeutically active compound and the ionic polymer are dissolved in a common solvent, e.g., dimethylacetamide, dimethylformamide, etc. The therapeutically active compound/polymer solution is added to cold (2°–5° C.) water adjusted to appropriate pH. The desired pH is dependent on the polymer used and is readily asertainablebly one skilled in the art. This causes the therapeutically active compound to microprecipitate in the polymer matrix. The microprecipitate is washed several times with aqueous medium until the residual solvent falls below an acceptable limit for that solvent. An "acceptable limit" for each solvent is determined pursuant to the International Conference on Harmonization (ICH) guidelines.

c) pH-Controlled Precipitation

In this process, microprecipitation of the therapeutically active compound in an ionic polymer is controlled by a drastic change in pH of the solution. The therapeutically active compound and the ionic polymer are dissolved at a high pH (e.g. pH~9) and precipitated by lowering the pH of the solution (e.g. to ~1), or vice versa. This method is particularly suitable for therapeutically active compounds that have pH-dependent solubility.

d) Hot Melt Extrusion Process

Mircroprecipitation of a therapeutically active compound in an ionic polymer having thermoplastic characteristics can be achieved by a hot melt extrusion process. The crystalline therapeutically active compound and the polymer are mixed in a suitable blender and fed continuously to a temperature-controlled extruder causing the therapeutically active compound to be molecularly dispersed in the molten ionic polymer. The resulting extrudates are cooled to room temperature and milled into a fine powder.

e) Supercritical Fluid Technology

The therapeutically active compound and an ionic polymer are dissolved in a supercritical fluid such as liquid nitrogen or liquid carbon dioxide. The supercritical fluid is then removed by evaporation leaving the therapeutically active compound microprecipitated in the polymer matrix. In another method, the therapeutic compound and an ionic polymer is dissolved in a suitable solvent. A microprecipitated powder can then be formed by spraying the solution in a supercritical fluid which acts as an antisolvent.

In another embodiment of the invention, pharmaceutical formulations may be prepared according to any one of the foregoing steps by the addition of a final step during which the compound/polymer complexes of the invention are formulated by methods well-known in the art.

In a preferred embodiment of the invention, the therapeutically active compound and the ionic polymer are dissolved in an organic solvent. Thereafter, the compound and the ionic polymer are co-precipitated relatively concurrently, preferably in aqueous solution, and preferably at a pH where, independently, neither the compound nor the polymer are soluble.

The organic solvent used to dissolve the therapeutically active compound and the ionic polymer should provide good solubility for both the poorly soluble compounds and the polymers used. These solvents include ethyl alcohol, methyl alcohol, acetone dimethyl sulfoxide, dimethyl acetamide, dimethyl formamide, N-methylpyrrolidone, Transcutol® (Diethylene glycol monoethyl ether, Gattefosse, Inc.), glycofural, propylene carbonate, tetrahydrofuran, polyethylene glycols and propylene glycols.

The pH selected to co-precipitate the therapeutically active compound and the ionic polymer depends on the solubility of each of the specific polymers and compounds being precipitated. One skilled in the art can easily ascertain the preferred pH for co-precipitation for each combination of polymer and therapeutically active compound. In a preferred embodiment wherein an anionic polymer selected from Eudragite® L100-55, Eudragit® L100 and Eudragit® S100 is used, the solution is precipitated at a pH lower than about 4. In another preferred embodiment wherein the cationic polymer Eudragit® E100 is used, the solution is precipitated preferably at a pH above 4.

The amounts of therapeutically active compound(s) and polymer necessary to achieve the stable, water-insoluble complex of the invention may vary depending upon the particular compound and ionic polymer(s) used, as well as the particular solvent(s) and precipitation parameters. By way of example, the compound may be present in the complex from about 0.1% to about 80%, by weight. Analogously, the polymer is typically present in the complex in not less than about 20% by weight. Preferably, the compound is present in the complex from about 30% to about 70% by weight, more preferably from about 40% to about 60% by weight. Most preferably, the compound is present in the complex at about 50% by weight. For a complex incorporating Compound I, the compound is present in the complex at about 30–70% by weight, most preferably at about 50% by weight.

Once the compound/polymer complex precipitates out of solution, the resulting complex can be recovered from the solution by procedures known to those skilled in the art, for example by filtration, centrifugation, washing, etc. The recovered mass can then be dried (in air, an oven, or a vacuum) and the resulting solid can be milled, pulverized or micronized to a fine powder by means known in the art. The powder form of the complex can then be dispersed in a carrier to form a pharmaceutical preparation.

The pharmaceutical preparations according to the invention can be administered to a subject by any route suitable for achieving the desired therapeutic result(s). Preferred routes of administration include parenteral and oral administration.

The pharmaceutical formulations according to the invention include a therapeutically effective amount of a therapeutically active compound. A therapeutically effective amount means an amount, at such dosages and for such periods of time, necessary to achieve the desired therapeutic result. Moreover, such amount must be one in which the overall therapeutically beneficial effects outweigh the toxic or undesirable side effects. A therapeutically effective amount of a compound often varies according to disease state, age and weight of the subject being treated. Thus, dosage regimens are typically adjusted to the individual requirements in each particular case and are within the skill in the art.

By way of example, for Compound I above, the appropriate daily dose for administration to an adult human weighing about 70 kg is from about 10 mg to about 10,000 mg, preferably from about 200 mg to about 1,000 mg, although the upper limit may be exceeded when indicated.

The daily dosage of the therapeutically active compound can be administered as a single dose, in divided doses, or for parenteral administration, it may be given as subcutaneous injection.

EXAMPLES

The following examples illustrate methods for making the water-insoluble compound/polymer(s) complexes of the present invention as well as pharmaceutical preparations incorporating said complexes.

For the examples reported herein, the therapeutically active compounds tested were Compounds I, II, Ill, IV and V, the structures for which are provided above. These compounds are practically insoluble in gastrointestinal fluids. Prior to the current invention, the crystalline, insoluble form of Compound I was the only stable form of this Compound that could be obtained.

GENERAL PROCEDURES

Procedure Applicable to Example 1
(Micronized Compound)

Compound I was micronized using a fluid energy mill to yield an average particle size of 10 microns. This procedure did not alter the crystalline form of the compound.

Procedure Applicable to Example 2
(Nanosized Compound)

A 10% suspension of Compound I was wet milled in aqueous medium containing 5% Klucel EF® (Hydroxypropylcellulose, Aqualon Corp.) as a protective colloid to prevent aggregation. The milling was performed in batch mode in a Dynomill for 24 hours using 0.25 mm glass beads as milling media. The average particle size of the resultant suspension was 700 nm and the residue obtained after drying the suspension demonstrated that the compound was present in crystalline form.

Procedure Applicable to Example 3
(Pluronic F 68 Dispersion)

A 10% dispersion of Compound I in 90% Pluronic F68 (polymer) was prepared using hot-melt technique. The compound was mixed into molten Pluronic F68 at 60° C. and the dispersion was then heated up to 180° C. to dissolve Compound I. The solution was cooled to room temperature to yield a solid mass. The powder x-ray diffraction ("XRD") pattern of the molten dispersion was similar to that for Pluronic F68. This XRD shows that Compound I was thus present in the solid dispersion in amorphous form. The solid dispersion obtained by this technique was further dispersed in aqueous medium prior to use in dosing animals.

Procedure Applicable to Examples 4–12 and 15–16
(Molecular Dispersion According to the Invention)

In accordance with the method of the invention, compounds I, II, IV or V and the specific polymer identified in each instance (i.e., Eudragit® L100-55, Eudragit® L100 or Eudragit® S100) were dissolved in dimethylacetamide. The resulting solution was then slowly added to cold (2–10° C.) aqueous solution at pH 2 causing the compound and the polymer to co-precipitate as an insoluble matrix wherein the compound was molecularly dispersed in the polymer. In each case, the precipitate was washed several times with cold (2–10° C.) aqueous solution at pH 2 until the residual dimethylacetamide was below 0.2%. The precipitate was dried in a forced air oven at 40° C. for 24 hours to a moisture level of below 2% and milled using a Fitz Mill® (Fitzpatrick) at slow speed using forward knives and size 0 screen into desirable particle sizes. The desired mean particle size was 90% particles in the size range 50–400 μm.

Procedure Applicable to Examples 13–14
(Compound III)

In accordance with the methods described above, Compound III and a specific polymer identified in each instance (i.e., Eudragit® L100-55, Eudragit® L100, Hydroxypropylmethylcellulose phthalate (HP-50) or Eudragit® S100) were dissolved in ethanol. The resulting solution was either dried in a vacuum oven at 40° C. for 24 hours until the weight loss on drying was less than 2%, or alternatively, the solution was spray dried. As a result of this process, the compound and the polymer co-precipitated as an insoluble complex wherein the compound was molecularly dispersed in the polymer. The resulting dried film was ground with a pestle/mortar and screened through 60 mesh screen.

Data

Table 1 below summarizes the results of Examples 1–16. Table 1 specifies the individual therapeutically active compounds and, where applicable, the compound/polymer complex that was prepared, the method of preparing the compound/polymer complex, and the physical characteristics of the resulting products from each example.

TABLE 1

Summary of Examples 1–14

| Example # | Composition (% w/w) | | Method of Preparation | Characterization of Resulting Product |
|---|---|---|---|---|
| 1 | Compound I (micronized) | 100% | Fluid energy mill | XRD-crystalline, Particle size: 50% ~10 μm |
| 2 | Compound I | 67% | Wet milling using 0.25 mm glass beads | XRD - crystalline, Particle size: 50% ~0.7 μm |
|   | Klucel EF ® | 33% | | |

TABLE 1-continued

Summary of Examples 1–14

Figure 4:
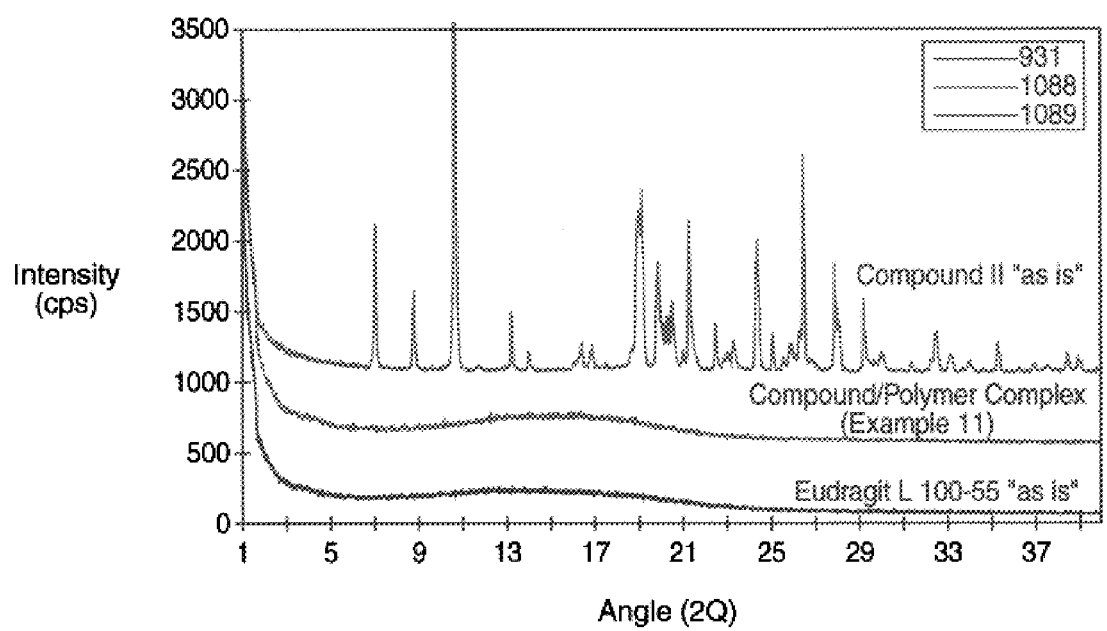
FIG. 4 is a powder x-ray diffraction pattern for Compound II "as is" and as compound/polymer complex (Example 11) after microprecipitation in accordance with the invention.
Figure 5:
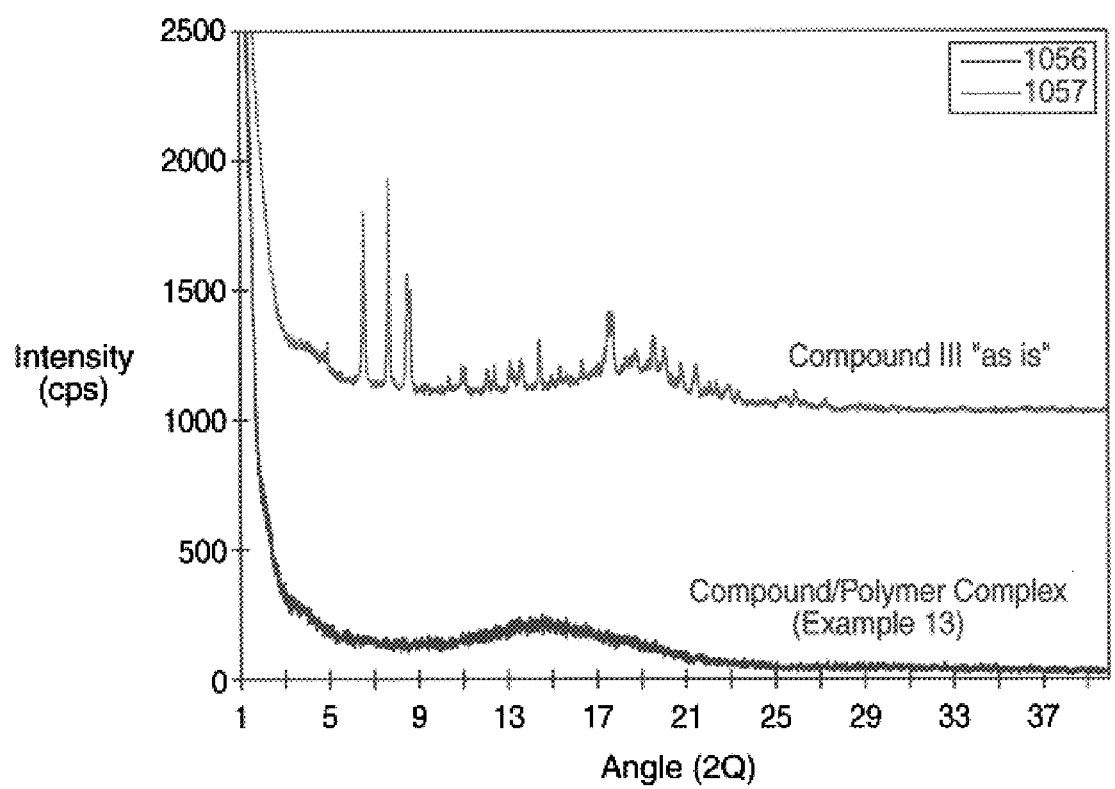
FIG. 5 is a powder x-ray diffraction pattern for Compound III "as is" and as compound/polymer complex (Example 13) after microprecipitation in accordance with the invention.
Figure 6:
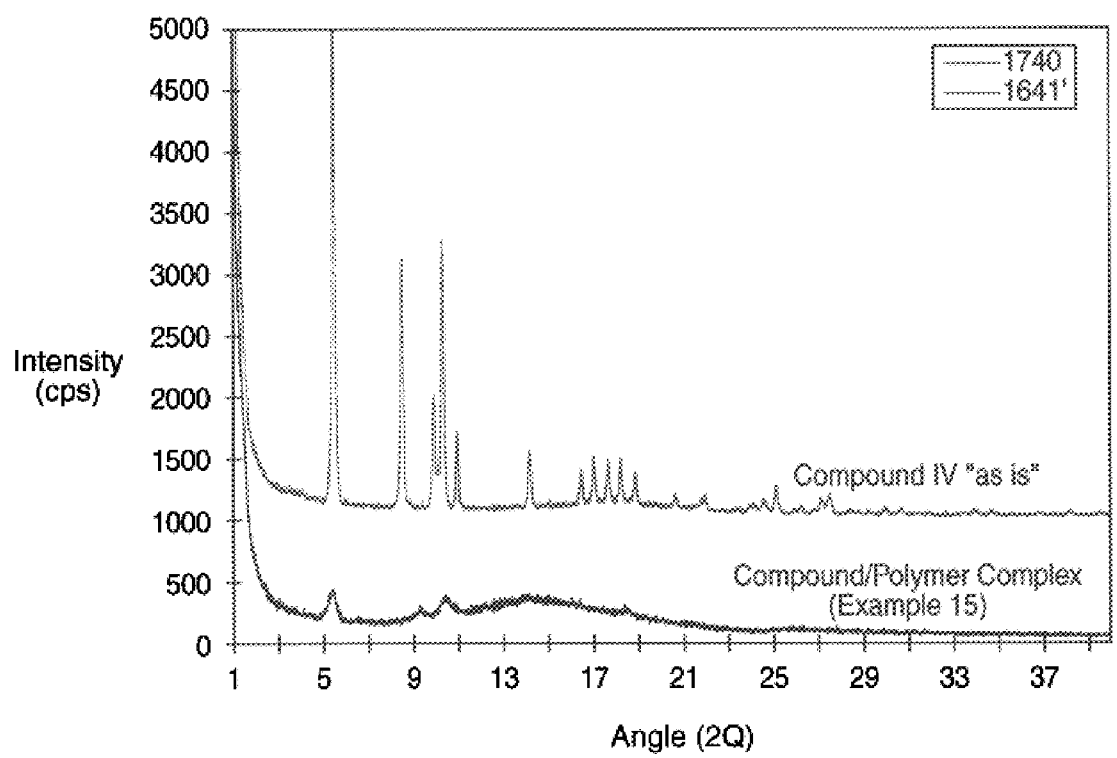
FIG. 6 is a powder x-ray diffraction pattern for Compound IV "as is" and as compound/polymer complex (Example 15) after microprecipitation in accordance with the invention.
Figure 7:
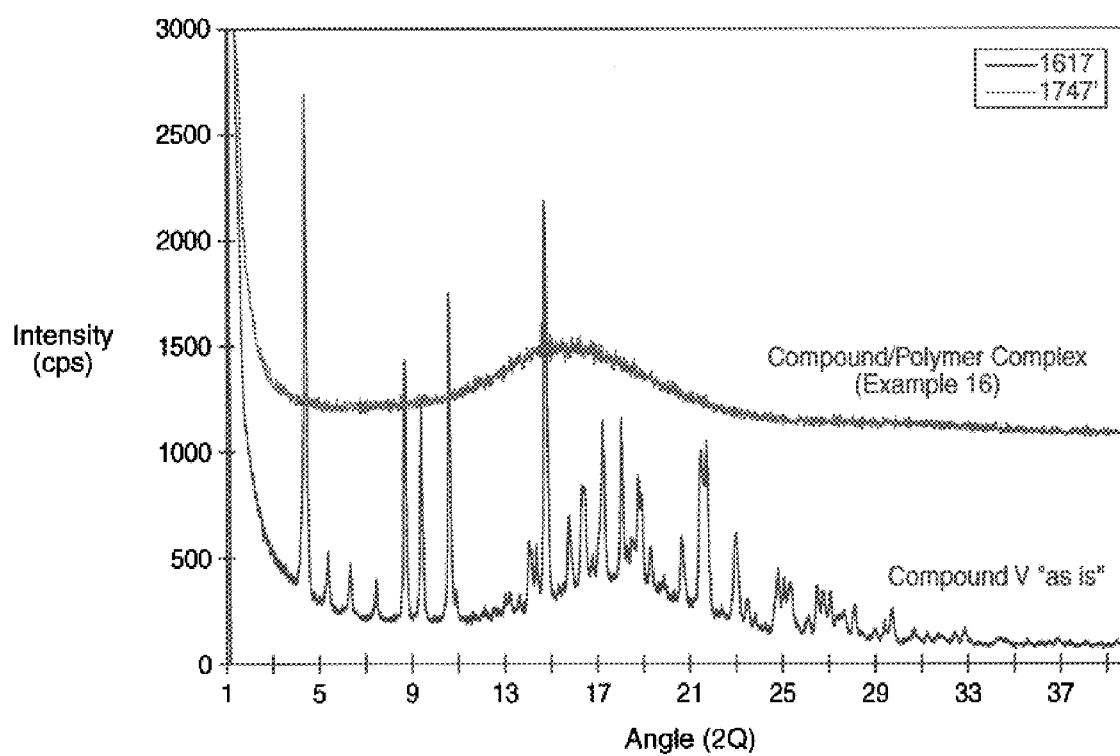
FIG. 7 is a powder x-ray diffraction pattern for Compound V "as is" and as compound/polymer complex (Example 16) after microprecipitation in accordance with the invention.

| Example # | Composition (% w/w) | | Method of Preparation | Characterization of Resulting Product |
|---|---|---|---|---|
| 3 | Compound I | 10% | Hot melt extrusion at about 180° C. | XRD - amorphous |
|   | Pluronic F68 | 90% | | |
| 4 | Compound I | 30% | Solvent-controlled precipitation | XRD - (FIGS.: 1 and 2) |
|   | Eudragit L 100-55 | 70% | | |
| 5 | Compound I | 50% | Solvent-controlled precipitation | XRD - Amorphous |
|   | Eudragit L 100-55 | 50% | | |
| 6 | Compound I | 70% | Solvent-controlled precipitation | XRD - Amorphous |
|   | Eudragit L 100-55 | 30% | | |
| 7 | Compound I | 30% | Solvent-controlled precipitation | XRD - Amorphous |
|   | Eudragit L 100 | 70% | | |
| 8 | Compound I | 50% | Solvent-controlled precipitation | XRD - Amorphous |
|   | Eudragit L 100 | 50% | | |
| 9 | Compound I | 15% | Solvent-controlled precipitation | XRD - Amorphous |
|   | Eudragit L100-55 | 42.5% | | |
|   | Eduragit S 100 | 42.5% | | |
| 10 | Compound I | 30% | Solvent-controlled precipitation | XRD - Amorphous |
|   | Eduragit L 100-55 | 35% | | |
|   | Eudragit S 100 | 35% | | |
| 11 | Compound II | 30% | Solvent-controlled precipitation | XRD - Amorphous (FIG. 4) |
|   | Eudragit L 100 | 70% | | |
| 12 | Compound II | 30% | Solvent-controlled precipitation | XRD - Amorphous |
|   | HP-50* | 70% | | |
| 13 | Compound III | 30% | Spray drying | XRD - Amorphous (FIG. 5) |
|   | Eudragit L 100 | 70% | | |
| 14 | Compound III | 50% | Spray drying | XRD - Amorphous |
|   | Eudragit L 100 | 50% | | |
| 15 | Compound IV | 20% | Solvent-controlled precipitation | XRD - Amorphous (FIG. 6) |
|   | Eudragit L 100 | 80% | | |
| 16 | Compound V | 30% | Solvent-controlled precipitation | XRD - Amorphous (FIG. 7) |
|   | Eudragit L 100 | 70% | | |

*Hydroxypropylmethylcellulose phthalate

As is shown in FIG. 1 and Table 1, the powder x-ray diffraction (XRD) pattern of the complex resulting in Example 4 (Table 1), that is when Compound I is included in an ionic polymer in accordance with the process of the current invention, it takes an amorphous form.

Table I and FIGS. 4–7 also show that the methods of the present invention are useful in rendering Compound II, III, IV and V in amorphous form.

Figure 2:
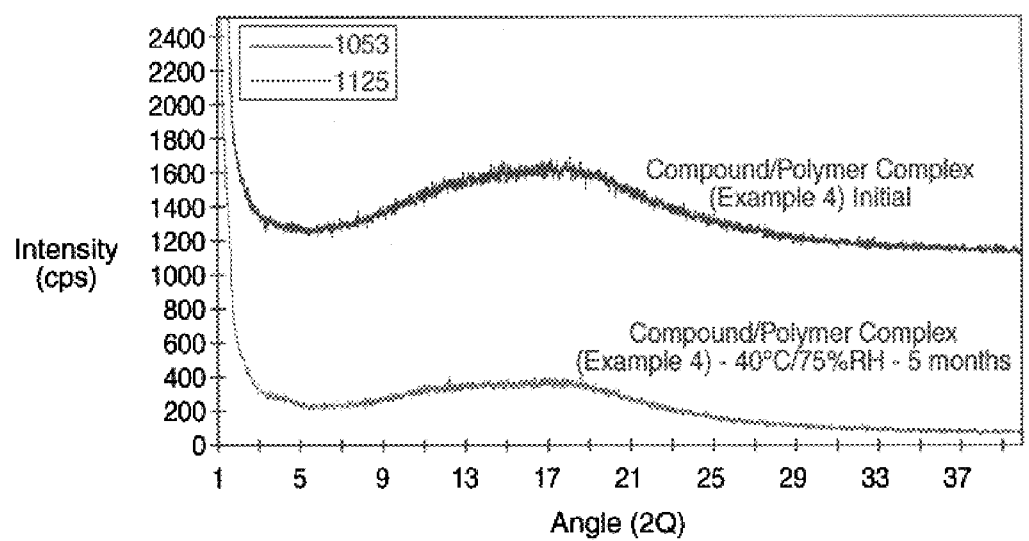
FIG. 2 is a powder x-ray diffraction pattern of samples from the compound/polymer complex of Example 4 exposed to accelerated stress conditions compared to unstressed (initial) compound/polymer complex.

The inclusion of Compound I in the ionic polymer protected the compound from external environmental effects such as moisture and heat. This result is demonstrated in FIG. 2, wherein it is shown, by powder x-ray diffraction, that Compound I embedded in the polymer maintained its amorphous properties even under accelerated storage conditions. The ability of the complex to maintain Compound I in amorphous form even after storage at accelerated stress condition is due to the high molecular weight (>80,000), high glass transition temperature (>50° C.) and insolubility in water of the polymer(s).

Furthermore, as is shown in Table 2 below, the bioavailability in dogs of Compound I when it is molecularly dispersed in an ionic polymer in accordance with the invention was unexpectedly higher than when the compound was administered to the animals in conventional forms (e.g. micronized and wet milled). Also shown in Table 2 are the bioavailability results obtained from solid dispersion of Compound I prepared by hot-melt method with Pluronic F68® (non-ionic water soluble polymer containing polyoxyethylene and polyoxypropylene chains, BASF). While the bioavailability of the Compound in this solid dispersion was better than when the compound was micronized or in wet mill suspension, the physical stability of the solid dispersion was not satisfactory for a pharmaceutical product as is evident by the reversion of compound to its crystalline form within one month of storage at ambient conditions. The above-described results demonstrate the unsuitability for preparation of a pharmaceutical product of the solid dispersion technique in non-ionic water soluble polymers.

TABLE 2

Bioavailability of Compound I in dogs after single oral dose administration (10 mg/kg)* for four animals (2 males and 2 females)

| Formulation | $AUC_{0-\infty}$/Dose (ng · h/ml)/(mg/kg) | % Bioavailability** |
|---|---|---|
| Micronized drug suspension (Example 1) | 29.5 ± 8.3 | 3.85 |
| Wet milled drug suspension (Example 2) | 86.1 ± 13.7 | 11.2 |
| Pluronic F68 Solid Dispersion*** (Example 3) | 532 ± 152 | 69.5 |
| Compound I/Polymer Complex (Example 4) | 529 ± 189 | 69.1 |
| Compound I/Polymer Complex (Example 5) | 560 ± 72 | 73.1 |
| Compound I/Polymer Complex (Example 6) | 588 ± 399 | 76.8 |
| Compound I/Polymer Complex (Example 7) | 604 ± 124 | 78.9 |
| Compound I/Polymer Complex (Example 8) | 768 ± 387 | 100.3 |
| Compound I/Polymer Complex (Example 9) | 415 ± 152 | 54.2 |
| Compound I/Polymer Complex (Example 10) | 264 ± 152 | 34.5 |

*Results are mean values (with standard deviations) for four animals (2 males and 2 females).
**Compared to Single Dose Intravenous Administration.
***Converts to crystalline form after exposure to 40° C., 75% RH, 1 wk, open condition.

Figure 3:
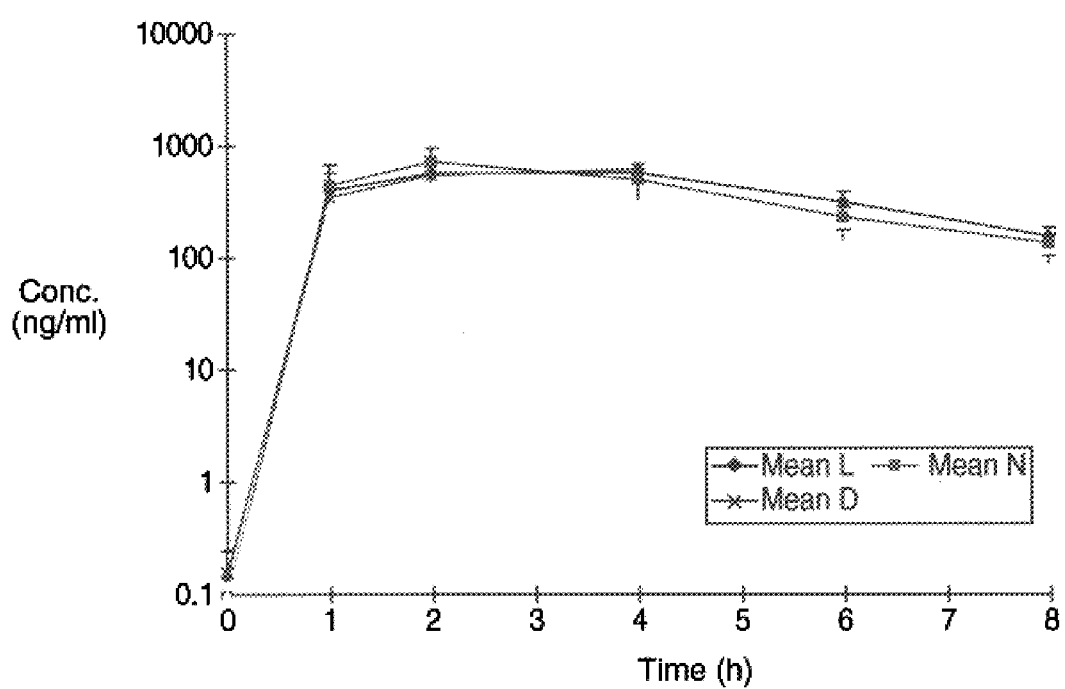
FIG. 3 is a plasma concentration profile in dogs of the compound/polymer complex of Example 4.

FIG. 3 shows plasma concentration-time profile of different batches of the compound/polymer complex produced in accordance to Example 4. The results of these tests (summarized in FIG. 3), show batch to batch reproducibility and consistency. Batch to batch reproducibility and consistency is an important aspect of any formulation that is intended for administration to human patients.

FIGS. 4–7 show that Compound II, III, IV and V also can be converted into amorphous form using this invention.

In summary, as is shown by the data in Tables 1 and 2 above and in FIGS. 1, 2, and 4–7, the powder x-ray diffraction patterns of the compound/polymer(s) complexes obtained in Examples 4–16 shows that molecularly dispersing a poorly soluble compound in an ionic polymer(s) according to the present invention converts the compounds into amorphous form and maintains excellent stability of the amorphous compound upon long-term storage.

We claim:

1. A pharmaceutical composition comprising a carrier and a water-soluble complex of a therapeutically active, stable amorphous compound selected from the group consisting of

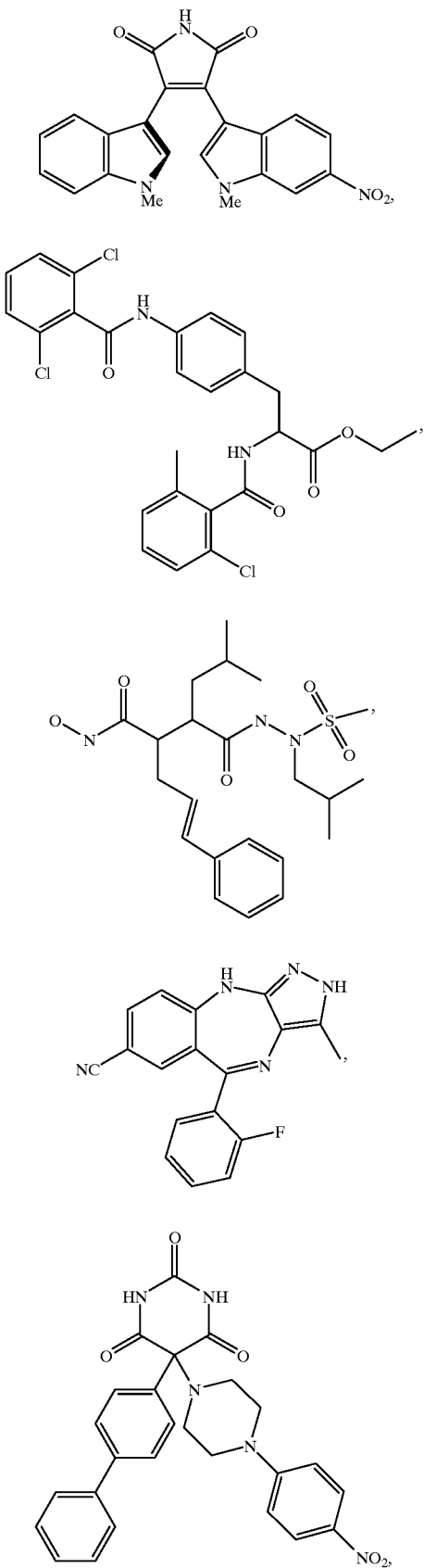

and a water-insoluble ionic polymer that has a molecular weight greater than about 80,000 D, a glass transition temperature equal to or greater than about 50° C. and is selected from the group consisting of polyacrylate, chitosan, carboxy vinyl polymers, polyvinly acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, wherein the therapeutically active compound is molecularly dispersed in the water-insoluble ionic polymer predominantly in amorphous form, as determined by powder X-ray diffraction, and is present in the resulting water-insoluble complex at not less than about 10%, by weight, and the water-insoluble ionic polymer is present in the water-insoluble complex at not less than about 20%, by weight.

2. The pharmaceutical composition of claim 1 wherein the ionic polymer is a polyacrylate.

3. The pharmaceutical composition of claim 1 wherein the polymer is a copolymer of methacrylic acid and ethyl acrylate or methacrylic acid and methyl methacrylate.

4. A water-insoluble complex comprising saquinavir and a water-insoluble ionic polymer that has a molecular weight greater than 80,000 D, a glass transition temperature equal to or greater than 50° C. and is selected from the group consisting of polyacrylate, chitosan, carboxy vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, wherein the therapeutically active, stable amorphous compound that is incorporated in the compound/polymer complex is predominantly in amorphous form, as determined by powder X-ray diffraction, and is present in the water-insoluble complex at not less that about 10%, by weight, and the ionic polymer is present in the complex at not less than about 20%, by weight.

5. The pharmaceutical composition of claim 1 wherein the solubility of the ionic polymer is pH dependent.

6. The pharmaceutical composition of claim 5 wherein the ionic polymer is insoluble at pH above about 4.

7. The pharmaceutical composition of claim 1 wherein the ionic polymer and the therapeutically active compound in its crystalline form are both relatively insoluble above pH of about 4.

8. The pharmaceutical composition of claim 5 wherein the ionic polymer is insoluble at pH below about 4.

9. The pharmaceutical composition of claim 1 wherein the ionic polymer and the therapeutically active compound in its crystalline form are both relatively insoluble at pH below about 4.

10. A pharmaceutical composition comprising a carrier and a water-insoluble complex of the compound

I

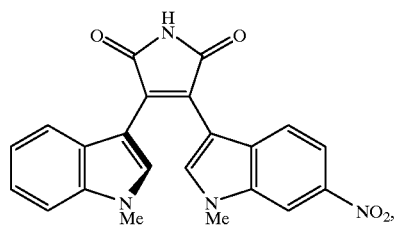

in stable, amorphous form, as determined by powder X-ray diffraction, and a water-insoluble ionic polymer that has a molecular weight greater than about 80,000 D, a glass transition temperature equal to or greater that about 50° C. and is selected from the group consisting of polyacrylate, chitosan, carboxy vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, wherein Compound I is present in the water-insoluble complex at not less that about 10%, by weight, and the water-insoluble ionic polymer is present in the water-insoluble complex at not less than about 20%, by weight.

11. The pharmaceutical composition of claim 10 wherein the therapeutically active compound is present in the water-insoluble complex at from about 10% to about 80%, by weight, of said complex.

12. The pharmaceutical composition of claim 11 wherein the therapeutically active compound is present in the water-insoluble complex at from about 30% to about 70%, by weight, of said complex.

13. The pharmaceutical composition of claim 12 wherein the ionic polymer is present in the water-insoluble complex at about 50%, by weight, and the therapeutically active compound is present at about 50%, by weight, of said complex.

14. A method for preparing a pharmaceutical formulation comprising a water-insoluble complex of a stable, amorphous therapeutically active compound selected from the group consisting of

I

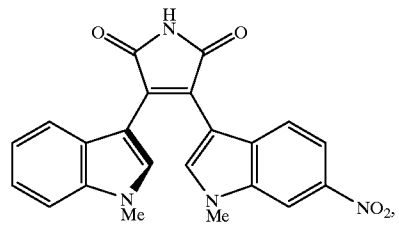

II

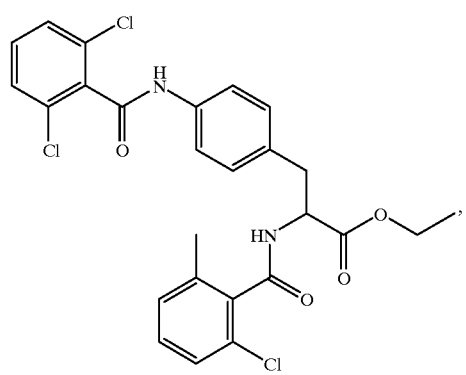

III

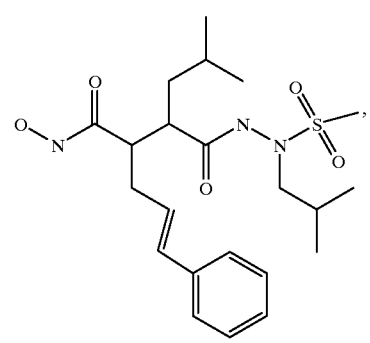

IV

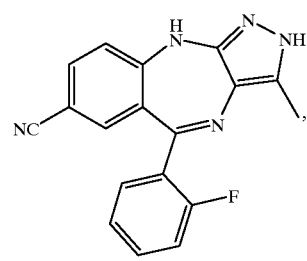

V

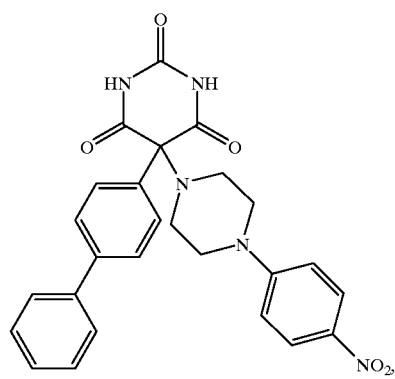

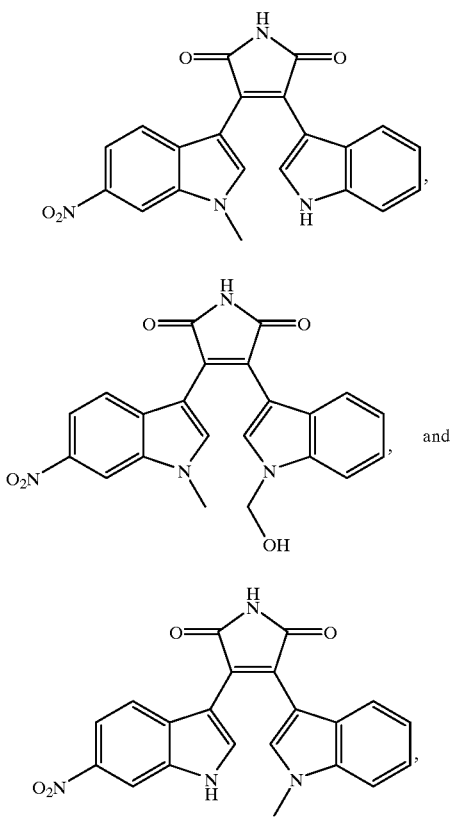

and an ionic polymer selected from the group consisting of polyacrylate, chitosan, carboxyl vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, comprising:

(a) dissolving the therapeutically active compound and ionic polymer in a suitable solvent;

(b) contacting the solution of step (a) with an aqueous solution at a pH in which the ionic polymer is poorly soluble thereby microprecipitating the therapeutically active compound and ionic polymer as a compound/polymer complex wherein the therapeutically active compound is present in the water-insoluble complex predominantly in amorphous form, as determined by powder X-ray diffraction, and is present in the complex at not less that about 10%, by weight, and the ionic polymer is present in the compound/polymer complex at not less than about 20%, by weight; and (c) combining the compound/polymer complex of step (b) above with a pharmaceutically acceptable carrier.

15. The method of claim 14, wherein in step (a), the therapeutically active compound and the ionic polymer are dissolved in a solvent selected from the group consisting of ethyl alcohol, methyl alcohol, dimethylsulfoxide, dimethylacetamide, dimethyl formamide, N-methylpyrrolidone, diethylene glycol monoethyl ether, glycofural, propylene carbonate, tetrahydrofuran, polyethylene glycol and propylene glycol.

16. The method in claim 14 wherein in step (b), microprecipitation is carried out by removing the solvent by spray drying or lyophilizing.

17. The method of claim 14 wherein in step (a), the insoluble therapeutically active and the ionic compound polymer are dissolved by adjusting the pH.

18. The methods of claim 14 wherein after step (b), residual solvent is removed.

19. The method of claim 18 wherein the residual solvent is removed by washing the compound/polymer complex.

20. The method of claim 18 wherein the residual solvent is removed by evaporation or drying.

21. The method of claim 20 wherein the residual solvent is removed by spray drying.

22. A method for preparing a pharmaceutical formulation comprising a water-insoluble complex of a stable, amorphous therapeutically active compound selected from the group consisting of

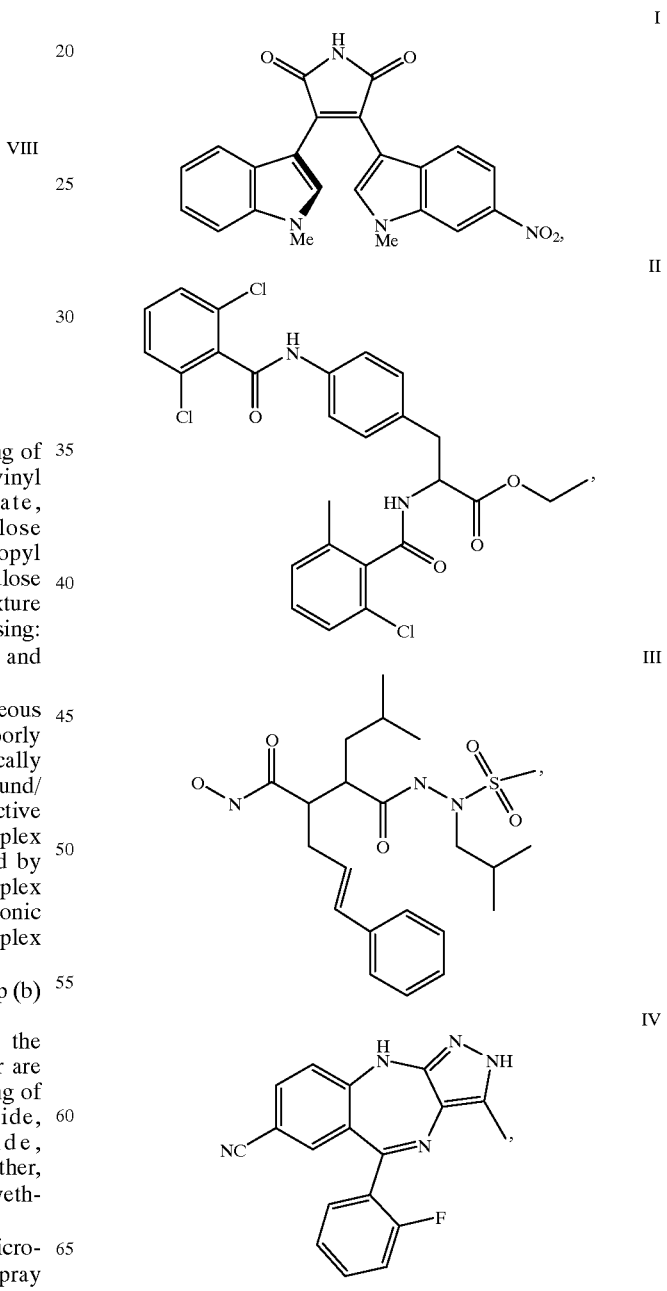

-continued

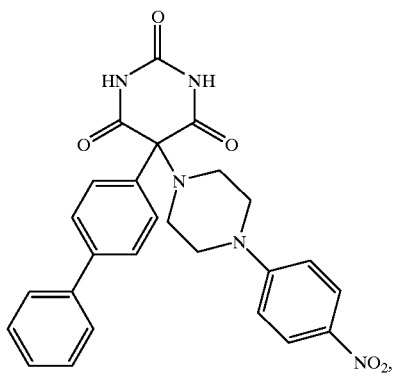
V

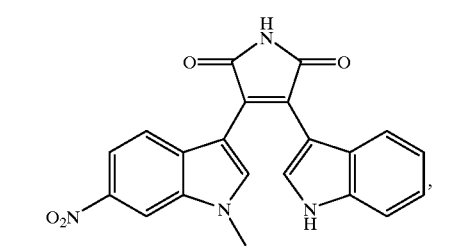
VI

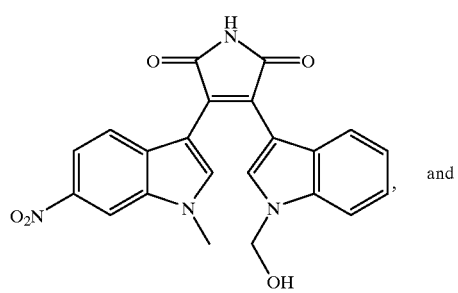
VII
and

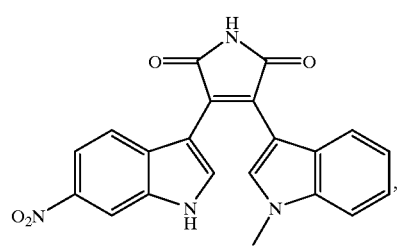
VIII and an ionic polymer selected from the group consisting of polyacrylate, chitosan, carboxy vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, comprising:

(a) dissolving the therapeutically active compound, in its crystalline form, and ionic polymer in an organic solvent;
(b) contacting the product of step (a) with an aqueous solution at a pH at which the ionic polymer and the therapeutically active compound will precipitate as a compound/polymer complex wherein the compound is present in the complex predominantly in amorphous form, as determined by powder X-ray diffraction, at not less than about 10%, by weight, and the ionic polymer is present in the complex at not less than about 20%, by weight;
(c) washing the compound/polymer complex;
(d) drying the compound/polymer complex; and
(e) combining the washed and dried compound/polymer complex of step (d) above with a pharmaceutically acceptable carrier.

23. The method of claim 22 wherein the ionic polymer is a polyacrylate.

24. A method for preparing a pharmaceutical formulation comprising a water-insoluble complex of a stable amorphous compound selected from the group consisting of

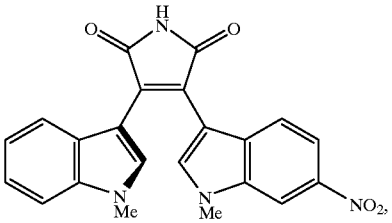
I

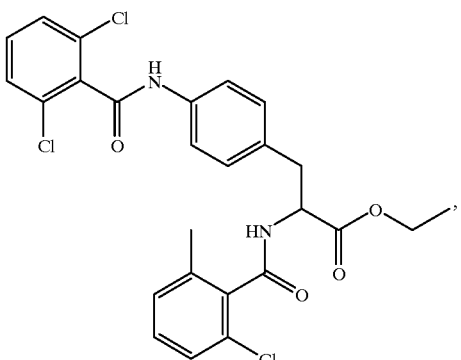
II

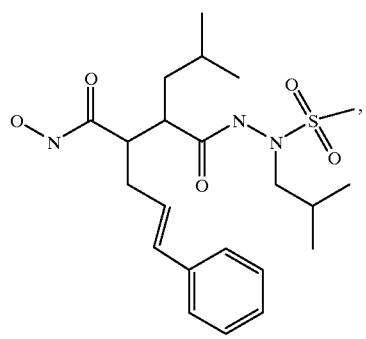
III

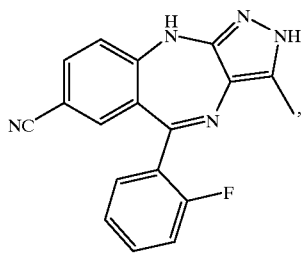
IV

-continued

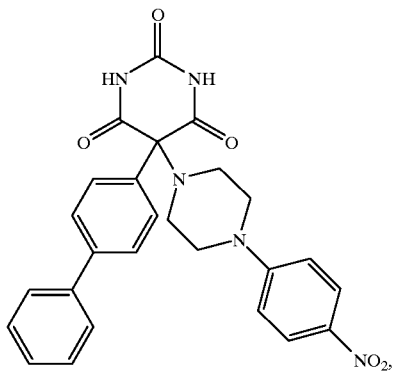

V

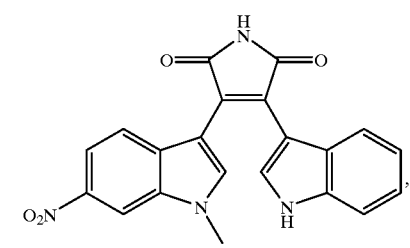

VI

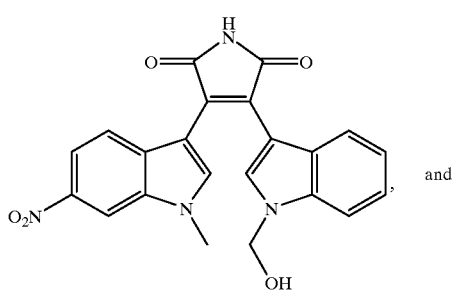

VII and

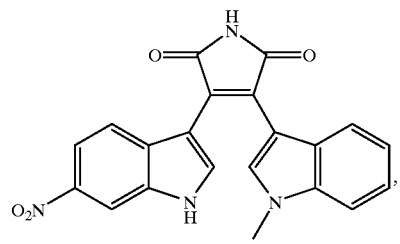

VIII and an ionic polymer selected from the group consisting of polyacrylate, chitosan, carboxy vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, comprising:
(a) dissolving the therapeutically active compound and the ionic polymer in a supercritical fluid;
(b) removing the supercritical fluid resulting in the microprecipitation of the therapeutically active compound in the polymer complex wherein the compound is present in the complex predominantly in amorphous form, as determined by powder X-ray diffraction, at not less than about 10%, by weight, and the ionic polymer is present in the complex at not less than about 20%, by weight; and
(c) combining the product of step (b) above with a pharmaceutically acceptable carrier.

25. The method of claim 24 wherein the supercritical fluid uses in step (a) is selected from the group consisting of liquid nitrogen and liquid carbon dioxide.

26. The method of claim 24 wherein removal of the supercritical fluid in step (b) is accomplished by evaporation.

27. A stable, water-insoluble complex prepared by:
(a) dissolving the compound

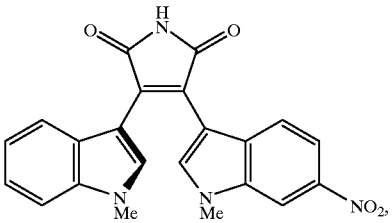

I and a water-insoluble ionic polymer having a molecular weight greater than 80,000 D, a glass transition temperature equal to or greater than 50° C., and being selected from the group consisting of polyacrylate, chitosan, carboxy vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, in a suitable solvent; and
(b) co-precipitating Compound I and the ionic polymer as a compound/polymer complex wherein Compound I is molecularly dispersed in amorphous form, as determined by powder X-ray diffraction, in the compound/polymer complex, and is present in the complex at not less than about 10%, by weight, and the ionic polymer is present in the complex at not less than about 20%, by weight.

28. The complex of claim 27 wherein precipitation in step (b) in effected by contacting the solution of step (a) with an aqueous solution at a pH in which the ionic polymer is poorly soluble.

29. A water-insoluble complex comprising a stable, amorphous compound selected from the group consisting of

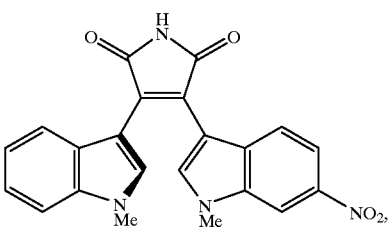

I

-continued

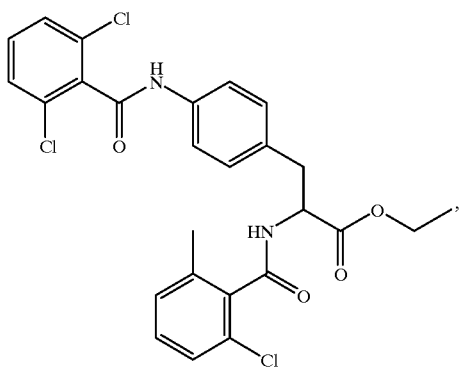
II

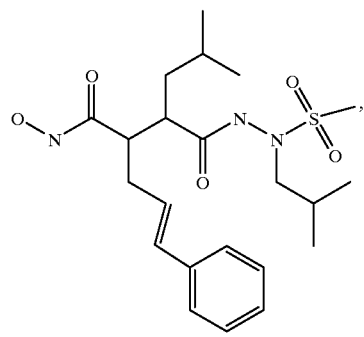
III

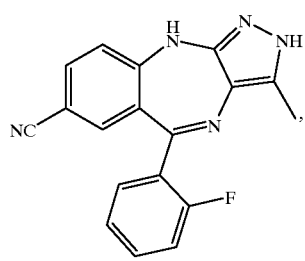
IV

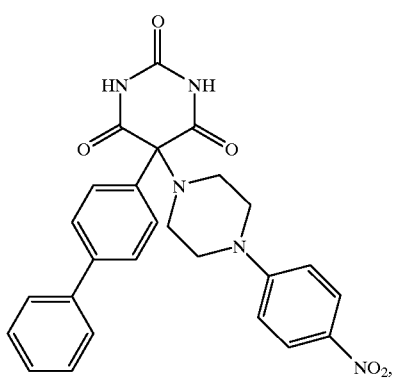
V

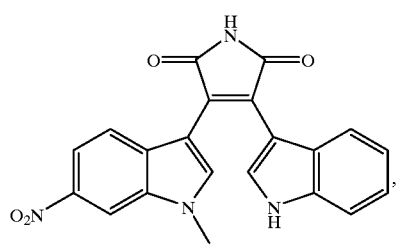
VI

-continued

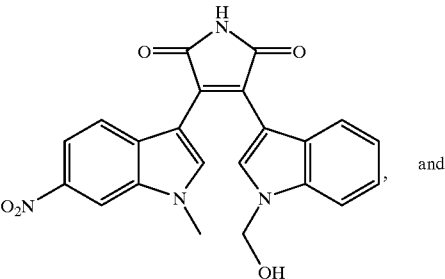
VII and

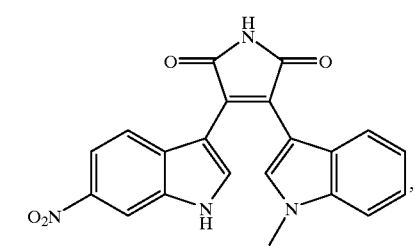
VIII and a water-insoluble ionic polymer that has a molecular weight greater than 80,000 D, a glass transition temperature equal to or greater than 50° C. and is selected from the group consisting of polyacrylate, chitosan, carboxy vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, wherein the therapeutically active, stable amorphous compound is incorporated in the compound/polymer complex predominantly in amorphous form, as determined by powder X-ray diffraction, and is present in the water-insoluble complex at not less that about 10%, by weight, and the ionic polymer is present in the complex at not less than about 20%, by weight.

30. The complex of claim 29 wherein the amorphous compound is poorly soluble in crystalline form.

31. A water-insoluble complex comprising the compound

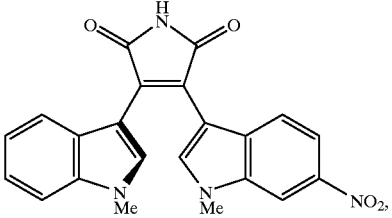
I in stable amorphous form and a water-insoluble ionic polymer that has a molecular weight greater than 80,000 D, a glass transition temperature equal to or greater than 50° C. and is selected from the group consisting of polyacrylate, chitosan, carboxy vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, wherein Compound I is incorporated in the compound/polymer complex in predominantly amorphous form, as determined by powder X-ray diffraction, and is present in the water-insoluble complex at not less that about 10%, by weight, and the ionic polymer is present in the complex at not less than about 20%, by weight.

32. A method for stabilizing an amorphous compound, the amorphous nature of which is determined by powder X-ray diffraction, selected from the group consisting of

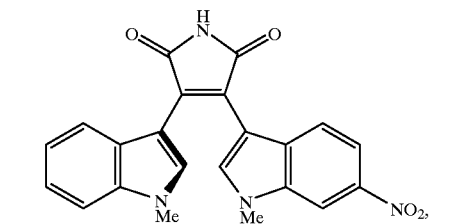

I

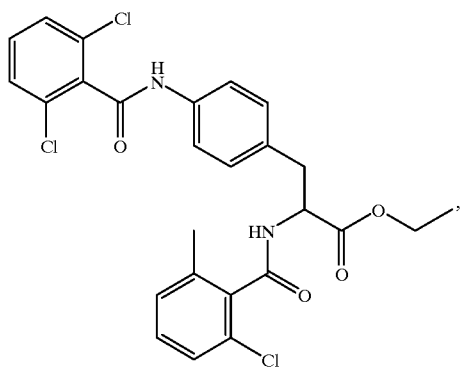

II

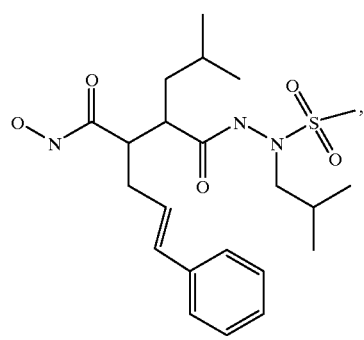

III

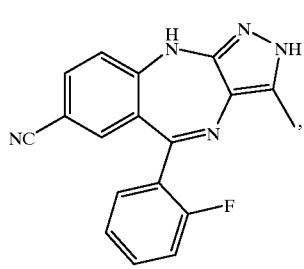

IV

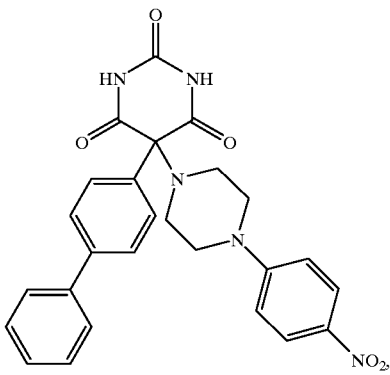

V

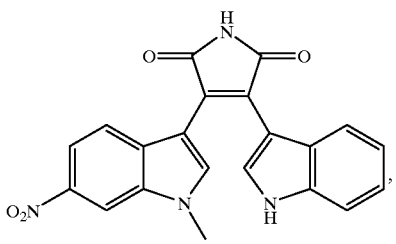

VI

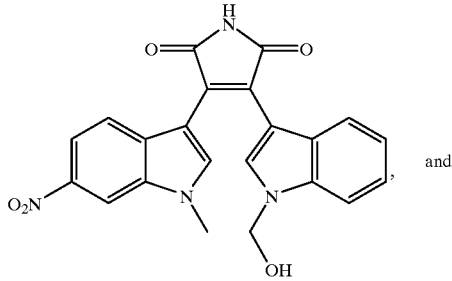

VII and

VIII comprising molecularly dispersing the compound in a water-insoluble ionic polymer that has a molecular weight greater than 80,000 D, a glass transition temperature equal to or greater than 50° C. and is selected from the group consisting of polyacrylate, chitosan, carboxy vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, resulting in a water-insoluble complex wherein the amorphous compound is present in the water-insoluble complex at not less that about 10%, by weight, and the ionic polymer is present in the complex at not less than about 20%, by weight.

33. A pharmaceutical composition comprising a carrier and a water-insoluble complex of saquinavir and a water-insoluble ionic polymer that has a molecular weight greater than about 80,000 D, a glass transition temperature equal to or greater than about 50° C. and is selected from the group consisting of polyacrylate, chitosan, carboxy vinyl polymers, polyvinyl acetate phthalate, cellulose acetate phthalate, polycyanoacrylates, hydroxypropylmethyl cellulose phthalate, cellulose acetate terphthalate, hydroxypropyl methyl cellulose acetate succinate, carboxy methyl cellulose and low substituted hydroxy propyl cellulose, or a mixture of two or more above-described ionic polymers, wherein the therapeutically active compound is molecularly dispersed in the water-insoluble ionic polymer predominantly in amorphous form, as determined by powder X-ray diffraction, and is present in the resulting water-insoluble complex at not less that about 10%, by weight, and the ionic polymer is present in the complex at not less than about 20%, by weight.

* * * * *

UNITED STATES PATENT AND TRADEMARK OFFICE
CERTIFICATE OF CORRECTION

PATENT NO. : 6,350,786 B1
DATED : February 26, 2002
INVENTOR(S) : Antonio A. Albano, Wantanee Phuapradit, Harpreet K. Sandhu and Navnit Hargovindas Shah It is certified that error appears in the above-identified patent and that said Letters Patent is hereby corrected as shown below:

Column 12,
Line 66, "a water-soluble complex" should read -- a water-insoluble complex --.

Signed and Sealed this

Twentieth Day of August, 2002

Attest:

JAMES E. ROGAN
Attesting Officer
Director of the United States Patent and Trademark Office